US00PP18519P3

(12) United States Plant Patent
Meilland

(10) Patent No.: US PP18,519 P3
(45) Date of Patent: Feb. 26, 2008

(54) SPRAY ROSE NAMED 'MEIHEVEN'

(50) Latin Name: *Rosa hybrida*
Varietal Denomination: Meiheven

(75) Inventor: Alain A. Meilland, Antibes (FR)

(73) Assignee: Meilland International S.A., Le Luc en Provence (FR)

( * ) Notice: Subject to any disclaimer, the term of this patent is extended or adjusted under 35 U.S.C. 154(b) by 32 days.

(21) Appl. No.: 11/542,233

(22) Filed: Oct. 4, 2006

(65) Prior Publication Data

US 2007/0083955 P1 Apr. 12, 2007

(30) Foreign Application Priority Data

Oct. 10, 2005 (EP) ..... 2005/1869

(51) Int. Cl.
*A01H 5/00* (2006.01)

(52) U.S. Cl. ..... Plt./101

(58) Field of Classification Search ..... Plt./101, Plt./134

See application file for complete search history.

*Primary Examiner*—Kent Bell
(74) *Attorney, Agent, or Firm*—Buchanan Ingersoll & Rooney PC

(57) ABSTRACT

A new and distinct variety of Spray rose plant is provided which abundantly forms on a nearly continuous basis in sprays attractive long-lasting yellow-green blossoms. The buds are substantially spherical in shape, the blossoms display a uniform and homogeneous appearance, and the vegetation is vigorous. The attractive green foliage contrasts nicely with the light blossom coloration. The new variety displays an excellent aptitude to forcing and is particularly well suited for cut flower production under greenhouse growing conditions.

1 Drawing Sheet

Figures 1, 2, 3, 4, 5, 6, 7, 8, 9, 10, 11, 12, 13, 14, 15, 16:
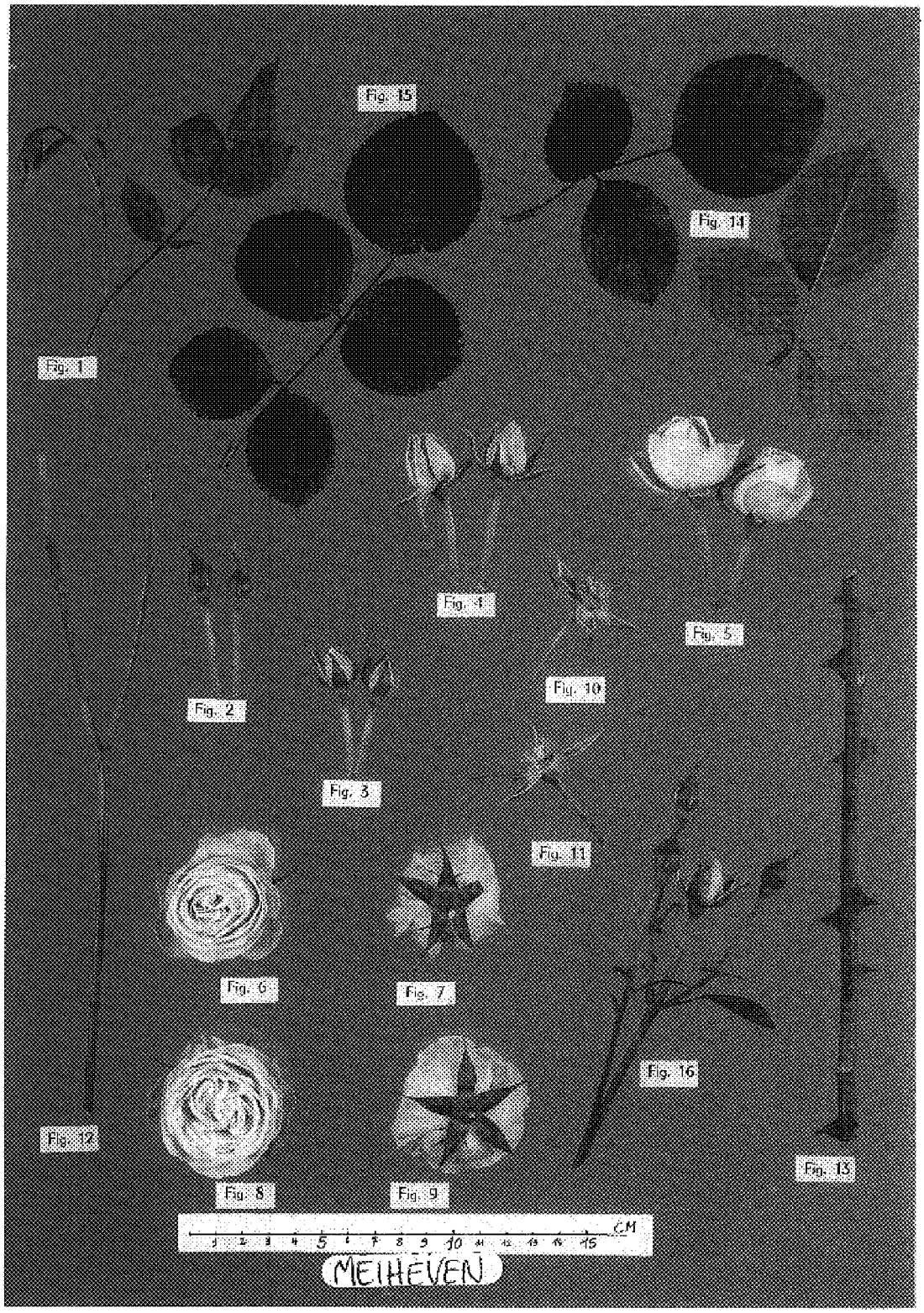

Botanical/commercial classification: *Rosa hybrida*/Spray Rose Plant.
Varietal denomination: cv. Meiheven.

SUMMARY OF THE INVENTION

The new variety of *Rosa hybrida* Spray rose plant was created by artificial pollination wherein two parents were crossed which previously had been studied in the hope that they would contribute the desired characteristics. The female parent (i.e., the seed parent) was the 'Meibondour' variety (non-patented in the United States). The male parent (i.e., the pollen parent) was the 'Keisupimi' variety (non-patented in the United States). The parentage of the new variety can be summarized as follows:

('Meibondour'×'Keisupimi').

The seeds resulting from the above pollination were sown and small plants were obtained which were physically and biologically different from each other. Selective study resulted in the identification of a single plant of the new variety.

It was found that the new Spray rose plant of the present invention:

(a) forms buds that are substantially spherical in shape,
(b) abundantly forms on a nearly continuous basis sprays of attractive long-lasting yellow-green blossoms,
(c) forms attractive green foliage that contrasts well with the light blossom coloration,
(d) displays an excellent aptitude to forcing, and
(e) is particularly well suited for cut flower production under greenhouse growing conditions.

No disease problem has been observed while grown in a greenhouse. The plant is precocious and the attractive blossoms display a uniform and homogenous appearance.

The new variety well meets the needs of the horticultural industry and can be grown to advantage under commercial greenhouse growing conditions.

The new variety can be readily distinguished from its ancestors upon an observation of the flower coloration. For instance, the 'Meibondour' variety displays yellow blossoms, and the 'Keisupimi' variety forms pink blossoms.

The new variety has been found to undergo asexual propagation in France by a number of routes, including budding, grafting, and the use of cuttings. Asexual propagation by the above-mentioned techniques in France has shown that the characteristics of the new variety are stable and are strictly transmissible by such asexual propagation from one generation to another.

The new variety has been named 'Meiheven'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately one year of age and were observed during September while budded on *Rosa indica major* understock and growing outdoors at Le Cannet des Maures, Var, France. Dimensions in centimeters are indicated at the bottom of the photograph.

FIG. 1—illustrates a specimen of a young shoot;

FIG. 2—illustrates specimens of two floral buds before the opening of the sepals;

FIG. 3—illustrates specimens of two floral buds at the opening of the sepals;

FIG. 4—illustrates specimens of two floral buds at the opening of the petals;

FIG. 5—illustrates specimens of two flowers in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates specimens of leaves with three leaflets—plan view—upper surface (upper left) and—under surface (lower right);

FIG. 15—illustrates a specimen of a leaf with five leaflets—plan view—upper surface; and FIG. 16—illustrates a cluster of buds.

DETAILED DESCRIPTION

The chart used in the identification of the colors is that of The Royal Horticultural Society (R.H.S. Colour Chart). The description is based on the observation of one-year-old plants during September while budded on *Rosa indica major* understock and growing in greenhouses at Le Cannet des Maures, Var, France.

Class: Spray.

Plant:

*Floral stems.*—When pruned to a height of 85 cm, floral stems having a length of approximately 90 cm commonly are produced.

*Height.*—Approximately 110 cm on average.

*Width.*—Approximately 80 cm on average.

Branches:

*Color.*—Young stems: near Green Group 143C. Adult wood: near Yellow-Green Group 146C.

*Thorns.*—On young stems: Small prickles: commonly absent. Long prickles: Configuration: rather straight, very longish pointed, curved downwards on the upper surface, and concave on the under surface with an ovate and narrow base. Quantity: approximately 8 on average on a stem length of 10 cm. Length: approximately 8 mm or more on average. Color: near Yellow-Green Group 145A. On adult stems: Small prickles: commonly absent. Long prickles: Configuration: rather straight, very longish pointed, curved downwards on the upper surface, and concave on the under surface with an ovate and narrow base. Quantity: approximately 4 on average on a stem length of 10 cm. Length: approximately 8 mm or more on average. Color: near Greyed-Orange Group 167A.

Leaves:

*Stipules.*—Smooth, adnate, pectinate, and narrow, approximately 1.8 cm in length, approximately 0.3 cm in width, near Green Group 137C in coloration on the upper surface, and near Yellow-Green Group 146B on the under surface.

*Petioles.*—Upper surface: near Yellow-Green Group 144A in coloration. Under surface: near Yellow-Green Group 144B in coloration. Length: approximately 3.7 cm for the terminal leaflet.

*Rachis.*—Upper surface: near Yellow-Green Group 144A in coloration. Under surface: near Yellow-Green Group 144B in coloration.

*Leaflets.*—Number: 3, 5, and 7 (most often). Shape: generally elliptic with an obtuse base and a pointed tip. Size: the terminal leaflets commonly are approximately 6.5 cm in length and approximately 4 cm in width on average. Serration: small and single (as illustrated). Texture: physically firm and relatively thick. Color (young foliage): Upper surface: near Green Group 137C. Under surface: near Green Group 138B. Color (adult foliage): Upper surface: near Green Group 137A. Under surface: near Yellow-Green Group 148C.

Inflorescence:

*Number of flowers.*—Pluriflorous, and commonly 5 to 7 blossoms in a spray per stem.

*Peduncle.*—Pubescent, near Yellow-Green Group 144A in coloration, approximately 4.8 cm in length, and near Yellow-Green Group 144A in coloration.

*Sepals.*—Upper surface: tomentose and near Green Group 138B in coloration. Under surface: glandular and near Yellow-Green Group 144A in coloration. Configuration: longish-pointed and narrow, approximately 1.9 cm in length on average, and approximately 0.6 cm in width on average at the widest point. Extensions: two sepals commonly possess no extensions and three sepals commonly possess very weak extensions.

*Buds.*—Shape: substantially spherical. Size: small. Length: approximately 2 cm on average. Width: approximately 1 cm on average at the widest point. Color: Upper surface: near Yellow-Green Group 150D. Under surface: near Yellow-Green Group 150D suffused with Yellow-Green Group 144B and 144C on the external petals as the calyx breaks. Basal petal spot: absent on both surfaces.

*Flower.*—Shape: cup-shaped. Diameter: approximately 4.5 cm on average. Color (in the course of opening): Upper surface: near Yellow-Green Group 150D. Under surface: near Yellow-Green Group 150D suffused with Yellow-Green Group 144B and 144C on the external petals. Basal petal spot: absent both surfaces. Color (when fully open): Upper surface: near Yellow-Green Group 150D. Under surface: near Yellow-Green Group 150D and suffused with Yellow-Green Group 144B and 144C on the external petals. Basal petal spot: absent on both surfaces. Color stability: very good. Fragrance: none. Lasting quality: very long, the blossoms commonly last approximately 14 to 16 days on average on the plant, and approximately 13 to 18 days on average when cut and placed in a vase. Petal number: commonly approximately 38 on average under normal growing conditions. Petal shape: round at base and tip. Petal size: commonly approximately 2.3 cm in length on average, and approximately 2.7 cm in width on average. Petal texture: consistent and somewhat firm. Petal arrangement: imbricated; and without petaloids. Petal drop: good with the petals commonly detaching cleanly. Stamen number: approximately 109 on average. Anthers: regularly arranged around the styles, approximately 0.2 cm in size on average, and near Greyed-Orange Group 163A in coloration. Pollen: present. Filaments: approximately 0.4 cm in length on average, and near Green-Yellow Group 1A in coloration. Pistils: approximately 62 on average. Stigmas: approximately 0.1 cm in size on average, and near Yellow Group 2A in coloration. Styles: approximately 0.4 cm in length on average, and near Green-Yellow Group 1D in coloration. Receptacle: smooth, pitcher-shaped in longitudinal section, approximately 0.7 cm in length on average, approximately 0.6 cm in width on average at the widest point, and near Yellow-Green Group 144A in coloration. Hips: none observed to date under greenhouse growing conditions.

Development:

*Vegetation.*—Strong and precocious.

*Blooming.*—Very abundant and nearly continuous.

*Resistance to diseases.*—No diseases have been observed to date while growing under greenhouse growing conditions.

*Aptitude to bear fruit.*—None observed during greenhouse growing conditions.

*Aptitude to forcing.*—Excellent.

I claim:

1. A new and distinct Spray rose plant characterized by the following combination of characteristics:

(a) forms buds that are substantially spherical in shape, (b) abundantly forms on a nearly continuous basis sprays of attractive long-lasting yellow-green blossoms, (c) forms attractive green foliage that contrasts well with the light blossom coloration, (d) displays an excellent aptitude to forcing, and (e) is particularly well suited for cut flower production under greenhouse growing conditions;

substantially as herein shown and described.

* * * * *

CM
MEIHEVEN